(12) United States Patent
Cote

(10) Patent No.: US 6,562,600 B1
(45) Date of Patent: May 13, 2003

(54) PRODUCTION OF CYCLIC ALTERNAN TETRASACCHARIDES FROM OLIGOSACCHARIDE SUBSTRATES

(75) Inventor: Gregory L. Cote, Edwards, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 30 days.

(21) Appl. No.: 09/891,123

(22) Filed: Jun. 25, 2001

(51) Int. Cl.$^7$ .................. C12P 19/18; C08B 31/00; C08B 38/00
(52) U.S. Cl. .................. 435/98; 435/99; 435/209; 435/210; 536/102; 536/123.12; 536/124; 536/125
(58) Field of Search .................. 435/98, 99, 209, 435/210; 536/102, 123.12, 124, 125

(56) References Cited

U.S. PATENT DOCUMENTS

| | | |
|---|---|---|
| 5,786,196 A | 7/1998 | Cote et al. |
| 5,888,776 A | 3/1999 | Cote et al. |
| 5,889,179 A | 3/1999 | Cote et al. |

FOREIGN PATENT DOCUMENTS

| | | | |
|---|---|---|---|
| JP | 09-084594 | * | 3/1997 |
| WO | WO 0190338 | | 11/2001 |

OTHER PUBLICATIONS

Caplus Abstract of JP 09–084594, 1997.*
Cote, G. L. et al "The hydrolytic transferase action of alternanase of oligosaccharides" Carbohydrate Res., vol. 332, pp. 373–379, 2001.*
Watanabe T., et al "Reversion product from D–glucose by purified Rhizopus niveus glucoamylase" pp. 18–21, 1969.*

* cited by examiner

Primary Examiner—James O. Wilson
Assistant Examiner—Leigh C. Maier
(74) Attorney, Agent, or Firm—John D. Fado; Randall E. Deck

(57) ABSTRACT

The cyclic tetrasaccharide, cyclo{-6)-α-D-Glcp-(1,3)-α-D-Glcp-(1,6)-α-D-Glcp-(1,3)-α-D-Glcp-(1-}, may be produced by alternanase hydrolysis of complex carbohydrates other than alternan. Panose, pullulan, α-D-Glcp-(1,6)-α-D-Glcp-(1,3)-D-Glc, and D-glucans having alternating α-(1,6) and α-(1,4) linkages, are all hydrolyzed by alternanase to produce this cyclic tetrasaccharide. In this process, the cyclic tetrasaccharide is produced by contacting a solution of one or more of the above-mentioned complex carbohydrates with an amount of alternanase under conditions effective for activity of the enzyme. The substrate panose used in the reaction may be produced from a variety of polysaccharides or oligosaccharides, including starch, maltose, maltodextrins, pullulan, and mixtures thereof.

13 Claims, No Drawings

PRODUCTION OF CYCLIC ALTERNAN TETRASACCHARIDES FROM OLIGOSACCHARIDE SUBSTRATES

BACKGROUND OF THE INVENTION

1. Field of Invention

This invention relates to a novel process for the production of cyclic alternan tetrasaccharide from alternanase using oligosaccharides as substrates.

2. Description of the Prior Art

Alternan, an extracellular D-glucan produced by *Leuconostoc mesenteroides* (Jeanes et al., 1954, J. Am. Chem. Soc., 76:5041–5052), and its lower molecular weight hydrolysis products have been previously described. Early studies of the alternan found that the compound was considerably resistant to microbial degradation and was also not attacked by enzymes that degrade starch, nigeran or pullulan (Cote, 1992, Carbohydrate Polymers, 19:249–252). The only enzymes that were reported to hydrolyze alternan to any significant extent were isomaltodextranases and alternanase. Of these, isomaltodextranases were not endo-hydrolases but rather exo-hydrolases or exo-dextranases. Two isomaltodextranases were examined for hydrolysis of alternan (referred to as B-1335 fraction S), the isomaltodextranases produced by *Arthrobacter globiformis* (Sawai et al., 1978, Carbohydrate Res., 66:195–205) and by an actinomycete Actinomadura (Sawai et al., 1981, Carbohydrate Res., 89:289–299). The authors concluded that the isomaltodextranases release mainly isomaltose units from the non-reducing ends of alternan chains that are terminated with an α-1,6-linked D-glucopyranosyl residues. Later, studies with *A. globiformis* isomaltodextranase purified in this laboratory according to Okada et al. (1988, J. Biol. Chem., 5:495–501) confirmed that this enzyme also was not capable of endo-hydrolytic cleavage of alternan, but functioned in an exo-fashion.

Alternanase was described more recently by Cote et al. as an endo-α-D-glucanase specific for alternan, having substantially greater activity toward alternan than dextran (U.S. Pat. Nos. 5,786,196, 5,888,776, and 5,889,179). This enzyme is produced and secreted extracellularly by a plurality of soil bacteria. Among the fractions present in the thinned alternan resulting from hydrolysis with alternanase are a previously unknown cyclic tetrasaccharide, cyclo{-6)-α-D-Glcp-(1,3)-α-D-Glcp-(1,6)-α-D-Glcp-(1,3)-α-D-Glcp-(1-} and derivatives thereof. This cyclic tetrasaccharide may be used as a metal salt complexing agent, a soluble, low- or non-caloric substitute for sucrose, and as bulking agents or extenders in foods and cosmetics.

SUMMARY OF THE INVENTION

I have now discovered that the cyclic tetrasaccharide, cyclo{-6)-α-D-Glcp-(1,3)-α-D-Glcp-(1,6)-α-D-Glcp-(1,3)-α-D-Glcp-(1-}, may be produced by alternanase hydrolysis of complex carbohydrates other than alternan. Surprisingly, panose, pullulan, α-D-Glcp-(1,6)-α-D-Glcp-(1,3)-D-Glc, and D-glucans having alternating α-(1,6) and α-(1,4) linkages, are not only hydrolyzed by alternanase, but the hydrolysis of these complex carbohydrates also produces the cyclic tetrasaccharide cyclo{-6)-α-D-Glcp-(1,3)-α-D-Glcp-(1,6)-α-D-Glcp-(1,3)-α-D-Glcp-(1-}. In this process, the cyclic tetrasaccharide is produced by contacting a solution of one or more of the above-mentioned complex carbohydrates with an amount of alternanase under conditions effective for activity of the enzyme. Furthermore, the substrate panose used in the reaction may be produced from a variety of polysaccharides or oligosaccharides, including starch, maltose, pullulan, and mixtures thereof.

In accordance with this discovery, it is an object of this invention to provide an improved, novel process for producing the cyclic tetrasaccharide cyclo{-6)-α-D-Glcp-(1,3)-α-D-Glcp-(1,6)-α-D-Glcp-(1,3)-α-D-Glcp-(1-}.

Another object of this invention is to provide a process for the production of the cyclic tetrasaccharide from common, readily available polysaccharides or oligosaccharides, particularly starch.

Other objects and advantages of this invention will become obvious from the ensuing description.

DETAILED DESCRIPTION OF THE INVENTION

The process of the invention produces the cyclic tetrasaccharide, cyclo{-6)-α-D-Glcp-(1,3)-α-D-Glcp-(1,6)-α-D-Glcp-(1,3)-α-D-Glcp-(1-}, which has the following structure (I):

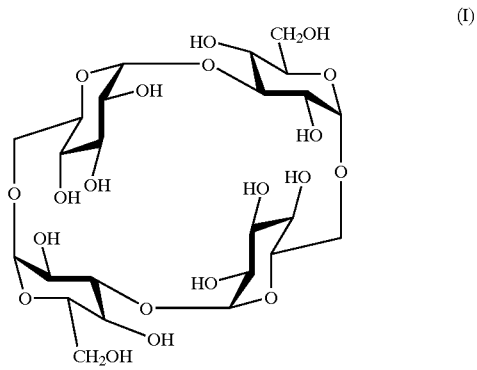

This structure is intended to show linkage only, and no particular conformation is implied. As noted above, this cyclic tetrasaccharide, as well as the enzyme alternanase, were described in the previous patents of Cote et al. (U.S. Pat. Nos. 5,786,196, 5,888,776, and 5,889,179, the contents of each of which are incorporated by reference herein). In the processes disclosed in those prior patents, the cyclic tetrasaccharide was formed by hydrolysis of alternan, a polysaccharide of alternating glucose units linked in an alternating α-1,3- and α-1,6-fashion, with alternanase.

In contrast with the previously described process, I have surprisingly found that not only will alternanase hydrolyze polysaccharides other than alternan, but it will hydrolyze selected complex carbohydrates to produce the same cyclic tetrasaccharide. Starting complex carbohydrates suitable for use herein as substrates for production of the cyclic tetrasaccharide include panose, pullulan, α-D-Glcp-(1,6)-α-D-Glcp-(1,3)-D-Glc, D-glucans having alternating α-(1,6) and α-(1,4) linkages, and mixtures thereof, with use of panose being preferred. However, although pullulan may be used, reaction rates and yields of the cyclic tetrasaccharide are significantly lower than those obtained using panose. The activity of alternanase toward these substrates is particularly unexpected as these polysaccharides do not contain the alternating α(1,3),α(1,6)-D-glucosidic linkage sequences previously thought to be necessary for alternanase activity.

In accordance with the process of this invention, a catalytically effective amount of alternanase may be contacted with one or more of the above-mentioned selected polysaccharide or oligosaccharide substrates in an aqueous solution under conditions effective to hydrolyze the polysaccharide. Alternanase generally retains hydrolytic activity over pH and temperature ranges between about 4.5 to 9 and about 0° to at least 50° C., respectively, with optima at about pH 7 and about 40° C. for the enzyme from strain NRRL B-21195. At a pH of 7.0, enzyme activity decreases rapidly as the temperature is increased to 60° C. The presence of calcium ions in the reaction mixture is required for optimal activity. Addition of the calcium binding agent EDTA has been found to inhibit activity.

Yields of cyclic tetrasaccharide will vary considerably with the particular substrate utilized, with optimal yields being obtained from use of panose. The extent of reaction may be controlled by terminating the reaction at any time. A variety of techniques which are conventional in the art may be used to stop the reaction, including heating to denature the enzyme, addition of inhibitors (e.g. EDTA), or adjusting the pH.

Following completion of the reaction, the cyclic tetrasaccharide produced may used in crude form, although it is preferably recovered from the reaction mixture in pure or substantially pure form. The particular technique for separation is not critical, and a variety of techniques are suitable for use herein. With the exception of the cyclic tetrasaccharide, the reaction products are all reducing sugars and thus may be removed using conventional ion-exchange resins. In the preferred embodiment, the cyclic tetrasaccharide may be selectively isolated from the other components of the reaction mixture by a single pass through a basic ion-exchange resin, which will bind the reducing sugars such as panose and maltose, but will allow the non-reducing cyclic tetrasaccharide to pass therethrough. Strong anionic exchange resins are particularly preferred for use herein, including, for example, AMBERLITE IRA-400 (Rohm & Haas, Philadelphia, Pa.) and DOWEX AG 1X (Dow Chemical, Midland, Mich.). Alternatively, the cyclic tetrasaccharide may be separated from the reaction mixture by chromatography, such as silica gel chromatography.

As starting materials in the reaction of the invention, the above-mentioned complex carbohydrates may be provided in substantially pure form or, in the alternative, they may be provided as a mixture or in impure form. Furthermore, although alternan does not interfere with the reaction and may be present, the reaction is preferably conducted substantially in the its absence.

In a preferred embodiment, the substrate panose is produced from reaction of a polysaccharide or oligosaccharide, such as starch, maltose, maltodextrins, pullulan, and mixtures thereof, whereupon it may be subsequently converted to the cyclic tetrasaccharide by action of alternanase. The particular process for the production of the panose is not critical, and a variety of techniques have been described which are suitable for use herein. Without being limited thereto, in one particularly preferred embodiment, maltose may be converted to panose by transglucosidation with known glucosyltransferase or glucosidase/transglucosidase preparations. For example, Hang and Woodams (1995, Biotech. Letters, 17:1335–1336, and 1997, Letters in Applied Microbiology, 24:43–46, the contents of each of which are incorporated by reference herein) disclosed that the glucosyl transferases of Aureobasidium species or *Aspergillus foetidus* (crude enzyme preparations or culture filtrate) or commercially available cytolase preparations all effectively converted maltose to panose. In another particularly preferred embodiment, starch or a maltodextrin or a mixture of maltodextrins may be hydrolyzed to maltose by action of α-amylase or β-amylase (alone or in combination with an α-[1,6]-glucosidase) such as described by Lehninger (Biochemistry, Second Edition, Worth Publishing, New York, 1975, pp. 264–265, the contents of which are incorporated by reference herein), which maltose may then be converted to panose as described above. Although pullulan may be directly hydrolyzed to the cyclic tetrasaccharide as disclosed hereinabove, reaction rates and yields are low. However, rates and yields may be increased significantly by hydrolyzing pullulan to panose by action of neopullulanase as described by Kuriki et al. (1992, J. Fermentation & Bioengineer., 73:198–202, the contents of which are also incorporated by reference herein), which panose is then converted to the cyclic tetrasaccharide by alternanase.

Panose for use as a substrate herein may also be produced from simpler saccharides, such as by reversion of D-glucose. In one embodiment, treatment of concentrated glucose syrups with acid or with α-glucosidase or glucoamylase will generate a mixture of di- and oligosaccharides, including panose.

Panose produced from a polysaccharide or oligosaccharide or from a simple saccharide in any of these techniques, may be converted to the cyclic tetrasaccharide by alternanase as described hereinabove. Moreover, the reaction of panose to cyclic tetrasaccharide may be conducted concurrently with the reaction(s) for generation of panose, or the reactions may be conducted separately. The skilled practitioner will recognize however, that when the reactions are conducted concurrently yields may be relatively lower, particularly if the conditions for optimal activity of the various enzymes used are different.

Production of alternanase utilized in this invention was described in Cote et al. (U.S. Pat. Nos. 5,786,196, 5,888,776, and 5,889,179) as mentioned hereinabove. In review, alternanase was originally isolated from soil bacteria that were selected for the ability to produce extracellular enzymes which hydrolyzed alternan in an endo-fashion, and seven strains of soil bacteria identified as belonging to the genus Bacillus were isolated which produced and secreted extracellular alternanase. All seven strains have been deposited under the Budapest Treaty in the United States Department of Agriculture, Agricultural Research Service culture collection in Peoria, Ill., and have been assigned deposit numbers NRRL B-21189, B-21190, B-21191, B-21192, B-21192, B-21193, B-21194 and B-21195. Of these, strain NRRL B-21195 produces the highest level of alternanase activity and is preferred. Alternanase produced from any of these strains will hydrolyze the polysaccharide substrates in the same manner to produce the cyclic tetrasaccharide.

Alternanase production may be accomplished by culture of any of the aforementioned bacterial strains, isolates or subcultures having the identifying characteristics of those strains, mutants of those strains capable of producing alternanase, or other isolates recovered by the screening procedure described hereinbelow, by conventional techniques under aerobic conditions that are effective to promote growth and alternanase production. Any number of well-known liquid or solid culture media may be used, although growth on liquid media is preferred as the enzyme is secreted into the media and recovery is simplified. Without being limited thereto, particularly preferred culture media include Brain-Heart Infusion Broth or Trypticase Soy Broth. Similarly, the media may contain a variety of carbon sources which will support growth and production of the enzyme, including but not limited to glucose, starch, maltose and alternan. The presence of alternan in the culture medium is not essential for production of the enzyme, although optimal alternanase production is achieved by addition of alternan thereto. The precise degree of enhancement is variable and is dependent upon the particular strain used. For example, production of the enzyme is greatly increased by addition of alternan when using strains NRRL B-21189, B-21190, B-21191, B-21192, B-21192, B-21193 and B-21194. In contrast, strain B-21195 is a constitutive producer of alternanase, and addition of alternan effects a less dramatic increase in alternanase production, approximately between 20 to 30%. The amount of alternan added to the media is not critical and may be readily determined by the practitioner skilled in the art. The bacteria will grow and produce alternanase over wide pH and temperature ranges, with a pH of about 7.0 and a temperature of about 30° C. being preferred.

Upon completion of the fermentation, typically between 24 to 96 hours, alternanase may be isolated or separated from the microorganisms using techniques conventional in the art, such as by centrifugation or filtration. As a practical matter, it is envisioned that commercial formulations of alternanase may be prepared directly from liquid culture medium from which cells have been removed in this manner, thereby obviating the need to further purify the enzyme.

Optionally, the alternanase remaining in the culture medium may be further concentrated and purified, particularly for applications demanding a high degree of purity where contamination by other enzymes, microbial products, monosaccharides, or culture media components may be undesirable. Suitable techniques for concentration and/or purification of alternanase may be readily determined by the practitioner skilled in the art and include, for example, dialysis, ion-exchange chromatography, and preferably HPLC size-exclusion chromatography and electrophoresis, particularly polyacrylamide-gel-electrophoresis (PAGE). Using these techniques, alternanase may be recovered in pure or substantially pure form. It is also envisioned that the enzyme may be formulated in conjunction with a suitable inert carrier or vehicle as known in the art. The skilled practitioner will recognize that such carriers must be compatible with the enzyme. Without being limited thereto, details of the preferred fermentation and separation procedures are described in Example 3 and in Biely et al. (1994, Eur. J. Biochem., 226:633–639, the contents of which are incorporated by reference herein).

For commercial applications, the cyclic tetrasaccharide may be used directly in crude form in the reaction mixture or, in the alternative, separated from the reaction mixture as described above. In either event, the cyclic tetrasaccharide may be used in a variety of applications, particularly as bulking agents or extenders in foods and cosmetics, as soluble, low- or non-caloric sucrose substitutes, or as metal salt complexing agents.

The cyclic tetrasaccharide may optionally be further modified, with such derivatives being useful in binding and complexing metal salts. Without being limited thereto, preferred derivatives include O-alkyl ethers, O-acyl esters, partially or fully sulfated esters, and particularly ionic carboxymethyl and diethylaminoethyl derivatives. These derivatives may be prepared at one or more sites on the cyclic tetrasaccharides using techniques conventional in the art, such as described by Yalpani (1988, Polysaccharides: Syntheses, Modifications and Structure/Property Relations, Elsevier Press, New York, pgs. 234–299) or Kennedy and White (Bioactive Carbohydrates: In Chemistry, Biochemistry and Biology, Halsted Press, New York, pgs. 63–65), the contents of each of which are incorporated by reference herein.

The following example is intended only to further illustrate the invention and is not intended to limit the scope of the invention which is defined by the claims.

EXAMPLE 1

Enzymes

*Leuconostoc mesenteroides* NRRL B-512 dextransucrase was a powdered preparation which had been stored at room temperature in a sealed bottle since 1952 (Tsuchiya et al., J. Bacteriol., 64:521–526). The activity was within 10% of that stated on the original label, despite storage for nearly 50 years. Endodextranase from Penicillium sp. was a gift from Novo Nordisk (Danbury, Conn.).

Alternanase from Bacillus sp. NRRL B-21195 was purified to electrophoretic homogeneity by affinity chromatography and isoelectrophoresis. The preparation used in reactions described here contained 0.018 mg·mL$^{-1}$ of purified protein (0.47 U·mg$^{-1}$) dissolved in 50 mM sodium 3-(N-morpholino)-2-hydroxypropane sulfonate buffer, pH 7.0, containing 50 mM KCl, 1 mM CaCl$_2$, and 1.5 mM NaN$_3$.

Carbohydrates

Maltose, nigerose, panose, and 1-O-(4-nitrophenyl) α-D-glucopyranoside were purchased from Sigma-Aldrich (St. Louis, Mo.). Pullulan was from Pfanstiehl Corp. (Waukegan, Ill.). All other compounds were reagent grade. Alternan was prepared as previously described [4]. Theanderose was purchased from Wako Fine Chemicals (Japan) and purified by gel filtration chromatography over Bio-Gel P-2 (Bio-Rad, Richmond, Calif.). 6-O-α-D-Glucopyranosyl α,α-trehalose and 6,6'-di-O-α-D-glucopyranosyl α,α-trehalose (Kurimoto et al., 1997, Biosci. Biotech. Biochem., 61:699–703) were generously provided by Dr. M. Kurimoto of Hayashibara Biochemical Laboratories (Okayama, Japan).

Isomaltose and isomaltotriose were isolated from an endodextranase hydrolyzate of commercial dextran (Jeanes et al., 1953, J. Amer. Chem. Soc., 75:5911–5915). The tetrasaccharide α-D-Glcp-(1,6)-α-D-Glcp-(1,6)-α-D-Glcp-(1,4)-D-Glc was prepared by the dextransucrase-catalyzed acceptor reaction with maltose (Killey et al., 1955, J. Amer. Chem. Soc., 77:3315–3318, and Castillo et al., 1992, Ann. N.Y. Acad. Sci., 672:425–430). The trisaccharide α-D-Glcp-(1,6)-α-D-Glcp-(1,3)-D-Glc was prepared in similar manner, using the B-512 dextransucrase acceptor reaction with nigerose. Likewise, 1-O-methyl α-isomaltoside was synthesized by acceptor reaction with 1-O-methyl α-D-glucopyranoside (Jones et al., 1956, J. Amer. Chem. Soc., 78:2499–2502). The tetrasaccharide α-D-Glcp-(1,3)-α-D-Glcp-(1,6)-α-D-Glcp-(1,4)-D-Glc was prepared using the acceptor reaction of alternansucrase with maltose (Cote and Robyt, 1982, Carbohydr. Res., 111:127–142). It was purified by gel-filtration chromatography, followed by preparative HPLC (Cote and Biely, 1994, Eur. J. Biochem., 225:641–648). 1-O-(4-Nitrophenyl) α-isomaltooligosaccharides were synthesized enzymatically from 1-O-(4-nitrophenyl) α-D-glucopyranoside using *L. mesenteroides* NRRL B-512 dextransucrase (Binder and Robyt, 1983, Carbohydr. Res., 124:287–299). 1-O-(4-Nitrophenyl) α-isomaltoside was recrystallized from water to eliminate traces of 4-nitrophenol and 1-O-(4-nitrophenyl) α-nigeroside. For preparative purposes, oligosaccharides were separated by size-exclusion chromatography over Bio-Gel P-2 (Bio-Rad, Richmond, Calif.).

Chromatography

Oligosaccharides were isolated from reaction mixtures by size-exclusion chromatography over Bio-Gel P-2, using either a 2.5×90 cm column or a 5×150 cm column eluted with water at room temperature. Fractions were analyzed for saccharide content by thin-layer chromatography (tlc). Oligosaccharides were separated on Whatman K5 silica gel plates which were developed with two ascents in nitroethane-acetonitrile-ethanol-water, 1:4:3:2 (vol.) (Cote and Biely, 1994, ibid). Compounds were detected with N-(1-naphthyl)ethylenediamine dihydrochloride (Bounias, 1980, Anal. Biochem., 106:291–295). 1-O-(4-Nitrophenyl) α-isomaltooligosaccharides were separated on silica gel plates with a single ascent in 85:15 acetonitrile-water. Detection was by quenching of the fluorescent indicator under UV light or by the method of Bounias (ibid).

Results

Action on α-D-Glcp-(1,6)-α-D-Glcp-(1,3)-D-Glc and Panose.

Alternanase acted on the trisaccharide α-D-Glcp-(1,6)-α-D-Glcp-(1,3)-D-Glc to yield D-glucose and the cyclic tetrasaccharide cyclo{→6)-α-D-Glcp-(1,3)-α-D-Glcp-(1,6)-α-D-Glcp-(1,3)-α-D-Glcp-(1→}. The identity of the cyclic product was confirmed by $^{13}$C NMR spectroscopy and methylation analysis. Alternanase acted on panose in a similar manner, giving rise to D-glucose and cyclo{→6)-α-D-Glcp-(1,3)-α-D-Glcp-(1,6)-α-D-Glcp-(1,3)-α-D-Glcp-(1→} as the two major products. The conversion of panose to cyclic tetramer plus glucose is clearly faster than the conversion of α-D-Glcp-(1,6)-α-D-Glcp-(1,3)-D-Glc to the same products. Although glucose and cyclic tetramer are the major products of both reactions, other products are also formed. Early in the reaction, two slower-migrating products appear. The faster-migrating of these eventually disappears, whereas the slower-migrating remains at a relatively constant level. At later stages of the reaction, isomaltose appears.

Action on α-D-Glcp-(1,3)-α-D-Glcp-(1,6)-α-D-Glcp-(1,4)-D-Glc.

The tetrasaccharide α-D-Glcp-(1,3)-α-D-Glcp-(1,6)-α-D-Glcp-(1,4)-D-Glc was rapidly hydrolyzed by alternanase. Initial products revealed by TLC included D-glucose, the trisaccharide α-D-Glcp-(1,3)-α-D-Glcp-(1,6)-D-Glc, and unknown oligosaccharides with $R_{glc}$ values in the range corresponding approximately to pentamers to heptamers. After digestion had proceeded to completion, these higher oligomers had vanished, leaving D-glucose and the trimer α-D-Glcp-(1,3)-α-D-Glcp-(1,6)-D-Glc as the major end-products. Traces of other oligosaccharides in the range of tetramers were also visible on tlc, but their identities could not be established.

Action on Cyclic Tetrasaccharide.

As previously reported (Cote and Biely, 1994, ibid), prolonged incubation of alternanase with cyclo{→6)-α-D-Glcp-(1,3)-α-D-Glcp-(1,6)-α-D-Glcp-(1,3)-α-D-Glcp-(1→} eventually results in the formation of isomaltose as well as traces of a slower-migrating product. Neither nigerose nor D-glucose is formed. This reaction is extremely slow compared to the formation of cyclic tetramer from alternan or panose. Action on 1-O-(4-nitrophenyl) αisomaltooligosaccharides.

Although little or no conversion of 1-O-(4-nitrophenyl) α-isomaltoside to other oligosaccharide products could be detected by thin-layer chromatography, measurable amounts of 4-nitrophenol were released by the action of alternanase. This reaction appears to be specific for the isomaltoside, as no 4-nitrophenol was released from 1-O-(4-nitrophenyl) α-D-glucopyranoside, 1-O-(4-nitrophenyl) α-isomaltotrioside, or 1-O-(4-nitrophenyl) α-isomaltotetraoside.

Activity on Other Saccharides.

When alternanase was incubated with the following isomaltosyl-containing saccharides at the same levels used for the conversion of panose and alternan, no products were detected by tlc: isomaltotriose, 1-O-methyl α-isomaltoside, 6-O-α-D-glucopyranosyl α,α-trehalose, 6,6'-di-O-α-D-glucopyranosyl α,α-trehalose, theanderose (α-D-Glcp-(1,6)-α-D-Glcp-(1,2)-β-D-Fruf), and α-D-Glcp-(1,6)-α-D-Glcp-(1,6)-α-D-Glcp-(1,4)-D-Glc. After prolonged treatment of pullulan with alternanase (approximately 2–3 weeks), traces of isomaltose and cyclic tetramer were discernible.

It is understood that the foregoing detailed description is given merely by way of illustration and that modifications and variations may be made therein without departing from the spirit and scope of the invention.

I claim:

1. A process for the production of the cyclic tetrasaccharide cyclo{-6)-α-D-Glcp-(1,3)-α-D-Glcp-(1,6)-α-D-Glcp-(1,3)-α-D-Glcp-(1-} comprising contacting a solution of a complex carbohydrate with an amount of alternanase under conditions effective for the conversion of said complex carbohydrate to said cyclic tetrasaccharide cyclo{-6)-α-D-Glcp-(1,3)-α-D-Glcp-(1,6)-α-D-Glcp-(1,3)-α-D-Glcp-(1-}, wherein said complex carbohydrate is selected from the group consisting of panose, -α-D-Glcp-(1,6)-α-D-Glcp-(1,3)-D-Glc, a D-glucan having alternating α-(1,6) and α-(1,4) linkages, and mixtures thereof.

2. The process of claim 1 wherein said complex carbohydrate comprises panose.

3. The process of claim 2, further comprising providing said panose by reacting a polysaccharide or oligosaccharide under conditions effective to produce panose.

4. The process of claim 3 wherein said polysaccharide or oligosaccharide is selected from the group consisting of starch, maltose, maltodextrin, pullulan and mixtures thereof.

5. The process of claim 4 wherein said polysaccharide or oligosaccharide is selected from the group consisting of starch, maltose, maltodextrin, and mixtures thereof.

6. The process of claim 2, further comprising providing said panose by reversion of D-glucose.

7. A process for the production of the cyclic tetrasaccharide cyclo{-6)-α-D-Glcp-(1,3)-α-D-Glcp-(1,6)-α-D-Glcp-(1,3)-α-D-Glcp-(1-} comprising:

(a) contacting a solution of a complex carbohydrate with an amount of alternanase under conditions effective for the conversion of said complex carbohydrate to said cyclic tetrasaccharide cyclo{-6)-α-D-Glcp-(1,3)-α-D-Glcp-(1,6)-α-D-Glcp-(1,3)-α-D-Glcp-(1-}, and (b) separating said cyclic tetrasaccharide from the reaction mixture, wherein said complex carbohydrate is selected from the group consisting of panose, pullulan, -α-D-Glcp-(1,6)-α-D-Glcp-(1,3)-D-Glc, a D-glucan having alternating α-(1,6) and α-(1,4) linkages, and mixtures thereof.

8. The process of claim 7 wherein said separating comprises ion exchange.

9. The process of claim 7 wherein said complex carbohydrate comprises panose.

10. The process of claim 9, further comprising providing said panose by reacting a polysaccharide or oligosaccharide under conditions effective to produce panose.

11. The process of claim 10 wherein said polysaccharide or oligosaccharide is selected from the group consisting of starch, maltose, maltodextrin, pullulan and mixtures thereof.

12. The process of claim 11 wherein said polysaccharide or oligosaccharide is selected from the group consisting of starch, maltose, maltodextrin, and mixtures thereof.

13. The process of claim 9, further comprising providing said panose by reversion of D-glucose.

* * * * *